(12) United States Patent
Nakamura et al.

(10) Patent No.: US 8,865,654 B2
(45) Date of Patent: Oct. 21, 2014

(54) EYE DROPS

(75) Inventors: Takahiro Nakamura, Ikoma (JP); Yuichiro Nakada, Ikoma (JP); Takashi Nagano, Ikoma (JP); Masatsugu Nakamura, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 100 days.

(21) Appl. No.: 13/394,194

(22) PCT Filed: Sep. 24, 2010

(86) PCT No.: PCT/JP2010/066488
§ 371 (c)(1),
(2), (4) Date: Mar. 5, 2012

(87) PCT Pub. No.: WO2011/037157
PCT Pub. Date: Mar. 31, 2011

(65) Prior Publication Data
US 2012/0165273 A1    Jun. 28, 2012

(30) Foreign Application Priority Data
Sep. 25, 2009  (JP) ................. 2009-220235

(51) Int. Cl.
| | | |
|---|---|---|
| A61K 38/00 | (2006.01) | |
| A61P 9/10 | (2006.01) | |
| A61P 27/02 | (2006.01) | |
| A61K 38/07 | (2006.01) | |
| A61K 9/00 | (2006.01) | |
| C07K 5/107 | (2006.01) | |
| C07K 5/103 | (2006.01) | |

(52) U.S. Cl.
CPC ............... *A61K 9/0048* (2013.01); *A61K 38/07* (2013.01); *C07K 5/1016* (2013.01); *C07K 5/1013* (2013.01)
USPC ........................................................ 514/20.8

(58) Field of Classification Search
None
See application file for complete search history.

(56) References Cited

U.S. PATENT DOCUMENTS

| 5,503,827 A | 4/1996 | Woog et al. |
|---|---|---|
| 7,232,881 B2 * | 6/2007 | Nishida et al. ................ 530/330 |
| 2005/0009752 A1 | 1/2005 | Nishida et al. |

FOREIGN PATENT DOCUMENTS

| EP | 0914827 A1 | 5/1997 |
|---|---|---|
| EP | 1462455 A1 | 9/2002 |
| JP | 10-17489 A | 1/1998 |
| JP | 2003-231695 A | 8/2003 |
| JP | 2006-117556 A | 5/2006 |

OTHER PUBLICATIONS

International Search Report for PCT/JP2010/066488 (in English) dated Nov. 2, 2010.
Naoyuki Yamada, "Promotion of Corneal Epithelial Wound Healing with a Tetrapeptide (SSSR) Derived from Insulin-like Growth Factor-1," *Journal of Japanese Ophthalmological Society*, Nov. 10, 2008, vol. 112, No. 11, pp. 984 to 993.
N. Yamada et al., "Promotion of corneal Epithelial Wound Healing by a Tetrapeptide (SSSR) Derived from IGF-1," *Invest. Ophthalmol. Vis. Sci.*, 2006, vol. 47, No. 8, pp. 3286 to 3292.
N. Chikamoto, "Efficacy of Substance P and Insulin-like Growth Factor-1 Peptides for Preventing Postsurgical Superficial," *Jpn. J. Ophthalmol.*, Oct. 2009, vol. 53, No. 5, pp. 464 to 469.
European Search Report which was mailed on Oct. 2, 2013 for corresponding European application No. EP 10818829.
English-language machine translation of Nakamura Masatane, New Peptide and Its Medicinal Use, JP 2003-231695 A (May 11, 2006).
English-language translation of Nakamura Masatane, New Peptide and Its Medicinal Use, JP 2003-231695 A (Aug. 19, 2003).

* cited by examiner

*Primary Examiner* — Thomas Heard
(74) *Attorney, Agent, or Firm* — Holtz, Holtz, Goodman & Chick, PC

(57) ABSTRACT

An eyedrop containing a peptide having an amino acid sequence represented by Ser-Ser-Ser-Arg ("SSSR"), or a pharmacologically acceptable salt thereof; and a peptide having an amino acid sequence represented by Phe-Gly-Leu-Met-$NH_2$ ("FGLM"), or a pharmacologically acceptable salt thereof. The concentration ratio between SSSR or a pharmacologically acceptable salt thereof and FGLM or a pharmacologically acceptable salt thereof is between 1/15 and 1/50. The concentration of SSSR or a pharmacologically acceptable salt thereof is between 0.001% and 0.3% (w/v) and the concentration of FGLM or a pharmacologically acceptable salt thereof is between 0.015% and 1.5% (w/V). The pH of the eye drop is maintained between 2.5 and 6.5.

4 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: Human

<400> SEQUENCE: 1

Ser Ser Ser Arg
1

<210> SEQ ID NO 2
<211> LENGTH: 4
<212> TYPE: PRT
<213> ORGANISM: Human

<400> SEQUENCE: 2

Phe Gly Leu Met
1

EYE DROPS

Cross-Reference to Related Applications

This application is a United States national phase application of International Application PCT/JP2010/066488 filed Sep. 24, 2010.

TECHNICAL FIELD

The present invention relates to an eye drop which contains a peptide having an amino acid sequence represented by Ser-Ser-Ser-Arg (hereinafter referred to as "SSSR") or a pharmaceutically acceptable salt thereof and a peptide having an amino acid sequence represented by Phe-Gly-Leu-Met-$NH_2$ (hereinafter referred to as "FGLM") or a pharmaceutically acceptable salt thereof, and is obtained by specifying the concentration ratio between the SSSR or a pharmaceutically acceptable salt thereof and the FGLM or a pharmaceutically acceptable salt thereof, the concentration of the SSSR or a pharmaceutically acceptable salt thereof, the concentration of the FGLM or a pharmaceutically acceptable salt thereof, and the pH range of the eye drop, thereby improving the effect on enhancing the healing of a corneal disorder and the stability of the active ingredients in the eye drop.

BACKGROUND ART

SSSR is a partial peptide of an insulin-like growth factor I (hereinafter referred to as "IGF-I"), and FGLM is a tetrapeptide at the C-terminal of Substance P (JP-A-2003-231695 and JP-A-10-17489).

JP-A-2003-231695 discloses that SSSR is found to be the minimum unit for the exhibition of the activity of IGF-I with respect to the activity of enhancing the healing of a wound and that combination use of a partial peptide of IGF-I such as SSSR and FGLM or Substance P exhibits an effect on enhancing the healing of a corneal disorder and the healing of a skin wound.

Further, JP-A-2003-231695 discloses an invention relating to a novel substance such as SSSR which is a partial peptide of IGF-I and the pharmaceutical use of a partial peptide of IGF-I such as SSSR and FGLM or Substance P in combination.

However, the formulation of an eye drop in which SSSR and FGLM are used in combination has not been fully studied.

SUMMARY OF THE INVENTION

Problems to be Solved by the Invention

With respect to the formulation of an eye drop in which two agents, SSSR and FGLM, are used in combination, it is an interesting subject to study the chemical properties of both SSSR and FGLM in detail and determine the concentration ratio between these medicaments, the concentration of each medicament, and the like so as to maximize the efficacy of a combination agent and minimize the occurrence of side effects thereof and also improve the storage stability of the eye drop in consideration of the distribution process of the eye drop or the variation in the usage of the eye drop.

Means to Solve the Problems

The present inventors made intensive studies, and as a result, they found the following fact and achieved the present invention. With respect to an eye drop containing SSSR or a pharmaceutically acceptable salt thereof and FGLM or a pharmaceutically acceptable salt thereof, the effect on enhancing the healing of a corneal disorder, which is the efficacy thereof, can be maximized, and the eye drop can be stably stored for a long period of time by:

1) adjusting the concentration ratio between the SSSR or a pharmaceutically acceptable salt thereof and the FGLM or a pharmaceutically acceptable salt thereof to a range of 1/15 to 1/50;

2) adjusting the concentration of the SSSR or a pharmaceutically acceptable salt thereof to a range of 0.001 to 0.3% (w/v);

3) adjusting the concentration of the FGLM or a pharmaceutically acceptable salt thereof to a range of 0.015 to 1.5% (w/v); and 4) adjusting the pH of the eye drop to a range of 2.5 to 6.5.

An eye drop comprising an acetate of a peptide having an amino acid sequence represented by Ser-Ser-Ser-Arg and a hydrochloride of a peptide having an amino acid sequence represented by Phe-Gly-Leu-Met-$NH_2$, wherein 1) the concentration ratio between the acetate of a peptide having an amino acid sequence represented by Ser-Ser-Ser-Arg and the hydrochloride of a peptide having an amino acid sequence represented by Phe-Gly-Leu-Met-$NH_2$ is in a range of 1/15 to 1/20;

2) the concentration of the acetate of a peptide having an amino acid sequence represented by Ser-Ser-Ser-Arg is in a range of 0.005 to 0.1%, (w/v);

3) the concentration of the hydrochloride of a peptide having an amino acid sequence represented by Phe-Gly-Leu-Met-$NH_2$ is in a range of 0.1 to 1% (w/v); and 4) the pH of the eye drop is in a range of 3.0 to 6.0.

That is, the present invention is directed to an eye drop containing SSSR or a pharmaceutically acceptable salt thereof and FGLM or a pharmaceutically acceptable salt thereof, and enables the maximization of the efficacy of a combination agent by studying the concentration ratio between the SSSR or a pharmaceutically acceptable salt thereof and the FGLM or a pharmaceutically acceptable salt thereof, the elimination of the occurrence of side effects of the medicaments by reducing the respective concentrations of the SSSR or a pharmaceutically acceptable salt thereof and the FGLM or a pharmaceutically acceptable salt thereof, and the long-term stable storage of the eye drop by studying the effect of the pH of the eye drop.

In the present invention, examples of the pharmaceutically acceptable salt include hydrochlorides, sulfates, phosphates, lactates, acetates, trifluoroacetates, formates, maleates, fumarates, oxalates, methanesulfonates, and p-toluenesulfonates. More preferred are acetates for the SSSR and hydrochlorides for the FGLM.

In the eye drop of the present invention, the concentration ratio between the SSSR or a pharmaceutically acceptable salt thereof and the FGLM or a pharmaceutically acceptable salt thereof is from 1/5 to 1/50, preferably from 1/15 to 1/50, more preferably from 1/15 to 1/20.

The results of the below-mentioned pharmacological effect test show that the effect on healing a corneal epithelial wound of a combination agent in which the SSSR or a pharmaceutically acceptable salt thereof and the FGLM or a pharmaceutically acceptable salt thereof are used in combination in the eye drop of the present invention is enhanced when the concentration ratio therebetween is in a range of 1/15 to 1/50, and in particular, the effect is maximized when the concentration ratio therebetween is in a range of 1/15 to 1/20.

The concentration of the SSSR or a pharmaceutically acceptable salt thereof in the eye drop of the present invention is from 0.001 to 0.3% (w/v), more preferably from 0.005 to 0.1% (w/v).

The concentration of the FGLM or a pharmaceutically acceptable salt thereof in the eye drop of the present invention is from 0.015 to 1.5% (w/v), more preferably from 0.1 to 1% (w/v).

The results of the below-mentioned pharmacological effect test show that when the concentration of the SSSR acetate and the concentration of the FGLM hydrochloride in the eye drop of the present invention are 0.001% (w/v) or more and 0.015% (w/v) or more, respectively, the combination agent exhibits an excellent efficacy. However, in general, when the concentration of a medicament is increased, side effects occur in some cases, and therefore, it is preferred to adjust the concentration of each medicament as low as possible.

The pH of the eye drop of the present invention is in a range of 2.5 to 6.5, preferably in a range of 3.0 to 6.0, more preferably in a range of 3.5 to 5.5. The results of the below-mentioned stability test show that an aqueous solution containing the SSSR acetate is stable at a pH of 6.5 or lower (in a range of 2.5 to 6.5), and an aqueous solution containing the FGLM hydrochloride is stable at a pH of 2.5 or higher (in a range of 2.5 to 7.0). Therefore, the eye drop containing the SSSR or a pharmaceutically acceptable salt thereof and the FGLM or a pharmaceutically acceptable salt thereof of the present invention can be stably stored for a long period of time in a pH range of 2.5 to 6.5.

The eye drop of the present invention can be prepared by a widely used method, and if necessary, a tonicity agent, a pH adjusting agent, or the like can be added.

Examples of the tonicity agent include concentrated glycerin, propylene glycol, polyethylene glycol, trehalose, sucrose, sorbitol, mannitol, sodium chloride, potassium chloride, calcium chloride, and magnesium chloride, and more preferred are sodium chloride and concentrated glycerin.

Examples of the pH adjusting agent include hydrochloric acid, citric acid, sodium citrate, phosphoric acid, sodium monohydrogen phosphate, sodium dihydrogen phosphate, potassium dihydrogen phosphate, glacial acetic acid, acetic acid, sodium acetate, sodium hydroxide, potassium hydroxide, boric acid, borax, monoethanolamine, sulfuric acid, sodium carbonate, and sodium hydrogen carbonate.

The eye drop of the present invention is used as a therapeutic agent for a corneal disorder, and examples of the corneal disorder include corneal ulcer, corneal epithelial defect, keratitis, and dry eye.

The frequency of the instillation of the eye drop of the present invention is appropriately determined according to the symptoms, age, dosage form, or the like. The eye drop may be instilled once to several times (for example, 1 to 6 times) a day in an amount of one to several drops at a time.

Effects of the Invention

As will be described in detail in the section of test mentioned below, the eye drop of the present invention can enhance the effect on healing a corneal epithelial wound of the combination agent when the concentration ratio between the SSSR acetate and the FGLM hydrochloride is adjusted to a range of 1/15 to 1/50, and in particular, the effect can be maximized when the concentration ratio therebetween is adjusted in a range of 1/15 to 1/20. In addition, when the concentration of the SSSR acetate is adjusted to 0.001% (w/v) or more and the concentration of the FGLM hydrochloride is adjusted to 0.015% (w/v) or more, an excellent efficacy can be exhibited, and further, when the pH of the eye drop of the present invention is maintained in a range of 2.5 to 6.5, the SSSR acetate and the FGLM hydrochloride can be stably stored for a long period of time.

MODE FOR CARRYING OUT THE INVENTION

Hereinafter, the results of various tests will be shown, however, these examples are for understanding the present invention better, and are not meant to limit the scope of the present invention.

1. Pharmacological Effect Test

A pharmacological effect test was carried out using test preparations shown below.

1-1. Preparation of Medicaments i) SSSR Acetate

A protected tetrapeptide (Z-Ser (OBzl)-Ser(OBzl)-Ser (OBzl)-Arg (NO$_2$)-OBzl) was synthesized by performing peptide chain elongation with Boc-Ser(OBzl)-OH by the Boc method using H-Arg(NO$_2$)-OBzl as a starting material of a C-terminal amino acid. Then, this protected tetrapeptide was subjected to deprotection by catalytic hydrogenation using palladium in the presence of acetic acid to give SSSR acetate.

ii) FGLM Hydrochloride

Protected dipeptides (Boc-Phe-Gly-OBzl and Boc-Leu-Met-NH$_2$) were synthesized from amino acid derivatives, Boc-Phe-OH and H-Gly-OBzl, and from amino acid derivatives, Boc-Leu-OH and H-Met-NH$_2$, respectively, by forming a peptide bond using a condensing agent. Then, these protected dipeptides were subjected to debenzylation by catalytic hydrogenation using palladium and peptide synthesis by the Boc method, whereby a protected tetrapeptide (Boc-Phe-Gly-Leu-Met-NH$_2$) was formed. Then, this protected tetrapeptide was subjected to deprotection using hydrogen chloride to give FGLM hydrochloride.

1-2. Preparation of Test Preparations

Test Preparation 1

The SSSR acetate and the FGLM hydrochloride were dissolved in phosphate buffered saline, whereby a test preparation 1 (eye drop) containing the SSSR acetate at 0.01% (w/v) and the FGLM hydrochloride at 0.005% (w/v) was prepared.

Test Preparations 2 to 8

Test preparations 2 to 8 were prepared in the same manner as the test preparation 1 except that the amount of the SSSR acetate and the amount of the FGLM hydrochloride in the test preparation 1 were changed to give the concentrations and the concentration ratio in each test preparation shown in Table 1.

1-3. Test Method and Results

Using a rat model of neuroparalytic keratopathy produced according to the method of Nagano et al. (Invest. Ophthalmol. Vis. Sci., 44, 3810-3815 (2003)), the effect on the healing of a corneal epithelial wound after exfoliation of the corneal epithelium was studied. Specifically, evaluation was carried out by the following method. After exfoliation of the corneal epithelium, each test preparation was instilled 6 times a day (5 μL per instillation) at 1.5-hour intervals. For the measurement of a wound area, fluorescein staining was carried out, and then, an image of the cornea was taken and an area stained with fluorescein was calculated using an image analysis system.

TABLE 1

|  | (A) SSSR acetate % (w/v) | (B) FGLM hydrochloride % (w/v) | Concentration ratio [(A)/(B)] | Pharmacological effect |
|---|---|---|---|---|
| Test preparation 1 | 0.01 | 0.005 | 1/0.5 | Δ |
| Test preparation 2 | 0.003 | 0.005 | 1/1.7 | Δ |
| Test preparation 3 | 0.001 | 0.005 | 1/5 | Δ |
| Test preparation 4 | 0.001 | 0.015 | 1/15 | ⊙ |
| Test preparation 5 | 0.003 | 0.05 | 1/17 | ⊙ |
| Test preparation 6 | 0.001 | 0.05 | 1/50 | ○ |
| Test preparation 7 | 0.0001 | 0.015 | 1/150 | Δ |
| Test preparation 8 | 0.000001 | 0.05 | 1/50000 | X |

⊙: A significant effect on extending the corneal epithelium was observed.
○: An effect on enhancing the healing of a corneal epithelial wound was observed.
Δ: A tendency to enhance the healing of a corneal epithelial wound was observed.
X: No effect on enhancing the healing of a corneal epithelial wound was observed.

1-4. Discussion

As is apparent from Table 1, in the case of the combination agents of the test preparations 4 to 6, the effect on healing a corneal epithelial wound is enhanced by the combination use of the SSSR acetate and the FGLM hydrochloride, and in particular, when the concentration ratio between the SSSR acetate and the FGLM hydrochloride is 1/15 and 1/17 (the test preparations 4 and 5), the effect is maximized. Accordingly, by adjusting the concentration ratio between the SSSR acetate and the FGLM hydrochloride to a range of 1/15 to 1/50, the concentration of the SSSR acetate to 0.001% (w/v) or more, and the concentration of the FGLM hydrochloride to 0.015% (w/v) or more, it can be expected that an excellent efficacy is exhibited.

2. Stability Test of Eye Drop 2-1. Preparation of Samples and Test Method

Each sample (100 mL, eye drop) containing the SSSR acetate at 0.003% (w/v) and the FGLM hydrochloride at 0.05% (w/v) was prepared at a pH in a range of 2.5 to 7.0 and stored at 40° C. The concentrations of the SSSR and the FGLM were measured by the HPLC method after 2 months storage, 3 months storage, and 6 months storage, and the residual ratios of the SSSR and the FGLM were determined, respectively.

2-2. Test Results

The residual ratio of the SSSR is shown in Table 2, and the residual ratio of the FGLM is shown in Table 3.

TABLE 2

| pH | Residual ratio of SSSR (40° C., 2 months) | Residual ratio of SSSR (40° C., 3 months) | Residual ratio of SSSR (40° C., 6 months) |
|---|---|---|---|
| 2.5 | 100% | 100% | 100% |
| 3.0 | 99% | 96% | 98% |
| 3.5 | 99% | 96% | 93% |
| 4.0 | 98% | 97% | 92% |
| 4.5 | 97% | 97% | 89% |
| 5.0 | 97% | 87% | 81% |
| 5.5 | 94% | 86% | 80% |
| 6.0 | 90% | 77% | 68% |
| 6.5 | 84% | 67% | 51% |
| 7.0 | 70% | 51% | 35% |

TABLE 3

| pH | Residual ratio of FGLM (40° C., 2 months) | Residual ratio of FGLM (40° C., 3 months) | Residual ratio of FGLM (40° C., 6 months) |
|---|---|---|---|
| 2.5 | 79% | 72% | 54% |
| 3.0 | 91% | 89% | 79% |
| 3.5 | 95% | 94% | 90% |
| 4.0 | 96% | 96% | 94% |
| 4.5 | 97% | 97% | 96% |
| 5.0 | 97% | 97% | 97% |
| 5.5 | 97% | 97% | 96% |
| 6.0 | 96% | 96% | 95% |
| 6.5 | 95% | 95% | 93% |
| 7.0 | 94% | 93% | 90% |

2-3. Discussion

It was found that even when the eye drop is stored at 40° C. for 6 months, 50 or more of the SSSR remains in a pH range of 2.5 to 6.5 (from Table 2), and 50%, or more of the FGLM remains in a pH range of 2.5 to 7.0 (from Table 3). Accordingly, in the eye drop containing the SSSR acetate and the FGLM hydrochloride of the present invention, by maintaining the pH of the eye drop in a range of 2.5 to 6.5, both SSSR acetate and FGLM hydrochloride can be stably stored for a long period of time.

3. PREPARATION EXAMPLES

As shown in Tables 4 and 5, eye drops 1 to 8 were prepared by a widely used method (100 mL each).

TABLE 4

|  | Eye drop 1 | Eye drop 2 | Eye drop 3 | Eye drop 4 |
|---|---|---|---|---|
| (A) SSSR acetate | 0.03 g | 0.009 g | 0.01 g | 0.01 g |
| (B) FGLM hydrochloride | 0.5 g | 0.15 g | 0.2 g | 0.5 g |
| Sodium chloride | 0.85 g | 0.87 g | 0.87 g | 0.85 g |
| Sodium hydroxide | q.s. | q.s. | q.s. | q.s. |
| Hydrochloric acid | q.s. | q.s. | q.s. | q.s. |
| Sterile purified water | q.s. | q.s. | q.s. | q.s. |
| Concentration ratio [(A)/(B)] | 1/17 | 1/17 | 1/20 | 1/50 |
| pH | 4 | 4 | 4 | 5 |

TABLE 5

|  | Eye drop 5 | Eye drop 6 | Eye drop 7 | Eye drop 8 |
|---|---|---|---|---|
| (A) SSSR acetate | 0.02 g | 0.04 g | 0.03 g | 0.1 g |
| (B) FGLM hydrochloride | 0.6 g | 0.8 g | 1.2 g | 1.5 g |
| Sodium chloride | 0.84 g | 0.81 g |  |  |
| Concentrated glycerin |  |  | 2.2 g | 1.9 g |
| Sodium hydroxide | q.s. | q.s. | q.s. | q.s. |
| Hydrochloric acid | q.s. | q.s. | q.s. | q.s. |
| Sterile purified water | q.s. | q.s. | q.s. | q.s. |
| Concentration ratio [(A)/(B)] | 1/30 | 1/20 | 1/40 | 1/15 |
| pH | 5 | 3.5 | 3.5 | 4 |

Industrial Applicability

The present invention provides an eye drop containing SSSR or a pharmaceutically acceptable salt thereof and FGLM or a pharmaceutically acceptable salt thereof, in which the efficacy of the eye drop has been maximized, the occurrence of side effects thereof has been minimized, and the storage stability thereof has been improved.

The invention claimed is:

1. An eye drop comprising (i) an acetate of a peptide having an amino acid sequence represented by Ser-Ser-Ser-Arg and (ii) a hydrochloride of a peptide having an amino acid sequence represented by Phe-Gly-Leu-Met-NH$_2$, wherein
   (a) a concentration ratio of the acetate of a peptide having an amino acid sequence represented by Ser-Ser-Ser-Arg to the hydrochloride of a peptide having an amino acid sequence represented by Phe-Gly-Leu-Met-NH$_2$ is 1/15 to 1/50;
   (b) the acetate of a peptide having an amino acid sequence represented by Ser-Ser-Ser-Arg has a concentration of 0.001 to 0.3% (w/v);
   (c) the hydrochloride of a peptide having an amino acid sequence represented by Phe-Gly-Leu-Met-NH$_2$ has a concentration of 0.015 to 1.5% (w/v); and
   (d) the eye drop has a pH of 2.5 to 6.5.

2. A method of stabilizing an eye drop having an excellent effect on enhancing the healing of a corneal disorder, wherein the an eye drop contains an acetate of a peptide having an amino acid sequence represented by Ser-Ser-Ser-Arg and a hydrochloride of a peptide having an amino acid sequence represented by Phe-Gly-Leu-Met-NH$_2$, comprising
   1) adjusting a concentration ratio of the acetate of a peptide having an amino acid sequence represented by Ser-Ser-Ser-Arg to the hydrochloride of a peptide having an amino acid sequence represented by Phe-Gly-Leu-Met-NH$_2$ to 1/15 to 1/50;
   2) adjusting the concentration of the acetate of a peptide having an amino acid sequence represented by Ser-Ser-Ser-Arg to 0.001 to 0.3% (w/v);
   3) adjusting the concentration of the hydrochloride of a peptide having an amino acid sequence represented by Phe-Gly-Leu-Met-NH$_2$ to 0.015 to 1.5% (w/v); and
   4) adjusting the pH of the eye drop to 2.5 to 6.5.

3. A method of stabilizing an eye drop having an excellent effect on enhancing the healing of a corneal disorder, wherein the eye drop contains an acetate of a peptide having an amino acid sequence represented by Ser-Ser-Ser-Arg and a hydrochloride of a peptide having an amino acid sequence represented by Phe-Gly-Leu-Met-NH$_2$, comprising
   1) adjusting a concentration ratio of the acetate of a peptide having an amino acid sequence represented by Ser-Ser-Ser-Arg to the hydrochloride of a peptide having an amino acid sequence represented by Phe-Gly-Leu-Met-NH$_2$ to 1/15 to 1/20;
   2) adjusting the concentration of the acetate of a peptide having an amino acid sequence represented by Ser-Ser-Ser-Arg to 0.005 to 0.1% (w/v);
   3) adjusting the concentration of the hydrochloride of a peptide having an amino acid sequence represented by Phe-Gly-Leu-Met-NH$_2$ to 0.1 to 1% (w/v); and
   4) adjusting the pH of the eye drop to 3.0 to 6.0.

4. The eye drop according to claim 1, wherein said concentration ratio is 1/15 to 1/17.

* * * * *